Figure 2:
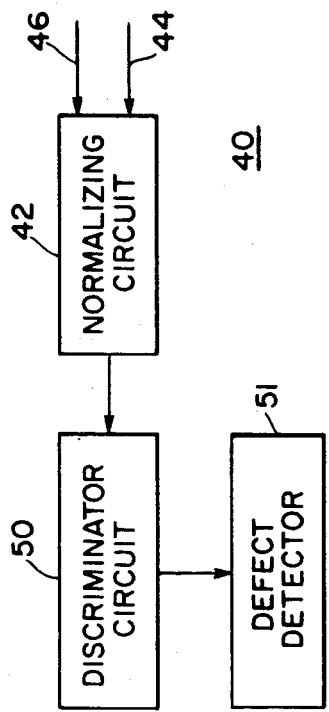

United States Patent [19]

Quackenbos et al.

[11] Patent Number: 4,794,264

[45] Date of Patent: Dec. 27, 1988

[54] SURFACE DEFECT DETECTION AND CONFIRMATION SYSTEM AND METHOD

[75] Inventors: George S. Quackenbos, Newburyport, Mass.; Jay L. Ormsby, Salem, N.H.; Eric T. Chase, Andover, Mass.; Sergey V. Broude, Acton, Mass.; Koichi Nishine, Westford, Mass.

[73] Assignee: QC Optics, Inc., Burlington, Mass.

[21] Appl. No.: 47,888

[22] Filed: May 8, 1987

[51] Int. Cl.$^4$ ............................................. C01B 21/88
[52] U.S. Cl. .................................. 250/563; 250/572; 356/237; 356/446
[58] Field of Search ............... 250/562, 563, 572; 356/446, 448, 429–431, 237

[56] References Cited

U.S. PATENT DOCUMENTS

| | | | |
|---|---|---|---|
| 4,172,666 | 10/1979 | Clarke | 250/563 |
| 4,184,082 | 1/1980 | Peoples | 356/446 |
| 4,492,477 | 1/1985 | Leser | 250/572 |
| 4,583,861 | 4/1986 | Yamaji et al. | 356/446 |
| 4,598,997 | 7/1986 | Steigmeier et al. | 250/572 |

Primary Examiner—Edward P. Westin
Assistant Examiner—Khaled Shami
Attorney, Agent, or Firm—Joseph S. Iandiorio; Douglas E. Denninger

[57] ABSTRACT

A surface inspection defect detection and confirmation technique in which a beam of radiation is directed at the surface to be inspected; the radiation scattered from the surface is separately sensed in the near-specular region indicative of a pit and in the far-specular region indicative of a flaw, the near-specular region signal and far-specular region signal are normalized, the near-specular component is discriminated, and the flaw signal is indicated as being a defect and not contamination when there is coincidence between the pit signal and flaw signal.

17 Claims, 4 Drawing Sheets

SURFACE DEFECT DETECTION AND CONFIRMATION SYSTEM AND METHOD

FIELD OF INVENTION

This invention relates to a surface defect detection and confirmation system and method, and more particularly to such a system and method which employ the coincidence of a sensed pit and sensed flaw to confirm that the flaw is a defect and not contamination.

BACKGROUND OF INVENTION

There are a number of different classes of surface flaws which may occur on smooth surfaces and which it is useful to detect and distinguish, especially in performing effective quality control. Such detection and differentiation of surface flaws is especially important, for example, with respect to the surfaces of nickel-plated aluminum substrates used in the manufacture of thin film magnetic media. One class of flaws is known as pits, which are local depressions with a diameter of from ten to several hundred microns, typically. The pits themselves may be smooth or contain breaks such as craters in their surfaces. A technique for detecting pits has been disclosed in a co-pending application for "Surface Pit Detection System and Method", Quackenbos et al., and is incorporated herein by reference. The second and third class of flaws, known as large defects and small defects, are closely related. Defects on the surface of rigid magnetic media may be the result of an impingement onto the surface or a tearing of material away from the surface. These types of defects can be very large scratches or gouges on the surface or very small (5 μm and smaller) tears or pricks on the surface. The large surface defects, because of their size and scattering properties, are readily distinguishable through sophisticated data processing. The small surface defects (5 μm and smaller) are not distinguishable since their scattering properties and physical size closely match that of adventitious surface contamination, which may be considered a fourth class of flaw.

SUMMARY OF INVENTION

It is therefore an object of this invention to provide an improved technique for detecting and distinguishing small as well as large surface defects from other flaws such as surface contamination.

The invention results from the realization that pits generally accompany flaws which are true defects but not flaws which are surface contamination, and thus the coincidence of a pit detection and flaw detection can be used to distinguish a defect from mere surface contamination or other flaws.

The invention features a surface defect detection and confirmation system including means for directing a beam of radiation to a surface and means for separately sensing radiation scattered from the surface in the near-specular region indicative of a pit and in the far-specular region indicative of a flaw, and providing signals representative thereof. There are means responsive to the means for sensing for normalizing the near-specular signal with respect to the far-specular signal. There are means responsive to the means for normalizing for discriminating the near-specular pit component from the normalized signal. Means responsive to coincidence of the pit signal and flaw signal indicate that the flaw is a defect and not a contamination.

In a preferred embodiment, the means for sensing may include lens means and a radiation source. The radiation provides a collimated beam which may be coherent and the source may be a laser. The system also includes means for providing relative motion between the beam and the surface to be inspected. The relative motion moves the beam and surface in two directions relative to one another and may include means for rotating the surface and translating the surface relative to the beam. The means for separately sensing may include a first sensor for sensing near-specular radiation and a second sensor for sensing far-specular radiation.

The means for normalizing may include a comparator. The comparator may receive a near-specular signal as a first polarity and a far-specular signal as a second, opposite polarity, and then sum the two signals. A comparator may subtract the near-specular signal from the far-specular signal. The means for discriminating may include a first detector circuit for detecting components of the first polarity of the normalized signal and a second detector circuit for detecting components of the second polarity of the normalized signal. The means for indicating may include an AND gate, and the AND gate may be responsive to the first and second detector circuits.

The invention also features a method of surface defect detection and confirmation in which an area of a surface to be inspected is irradiated. The radiation scattered from the surface is separately sensed in the near-specular region indicative of a pit and in the far-specular eegion indicative of a flaw. The near-specular pit signal is normalized with respect to the far-specular flaw signal. The near-specular pit component is discriminated from the normalized signal and there is given an indication that there is a defect and not contamination upon coincidence between the pit signal and the flaw signal.

DISCLOSURE OF PREFERRED EMBODIMENT

Figure 3:
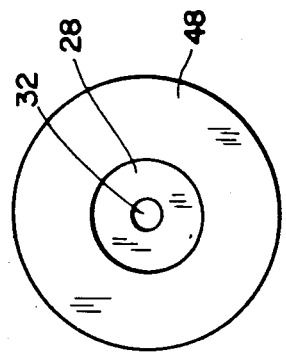
Figure 1:
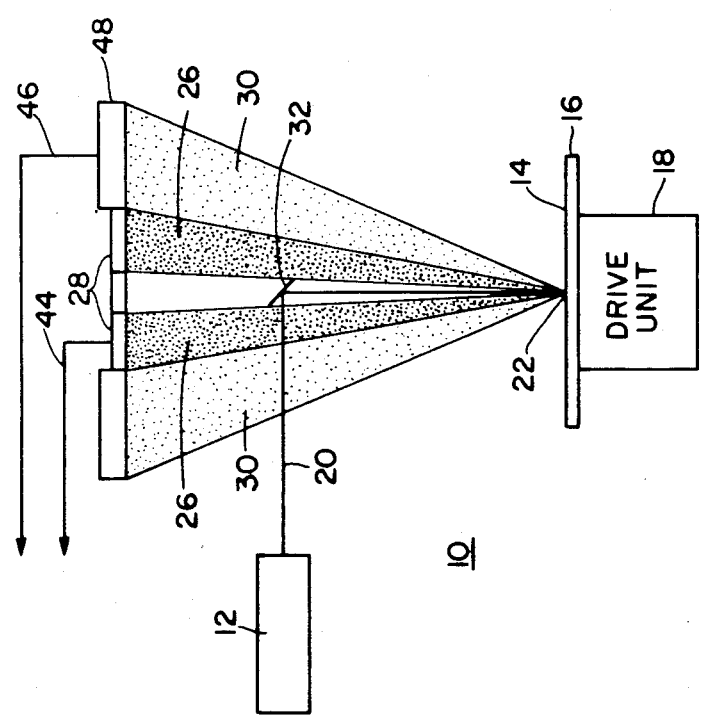
Figure 4:
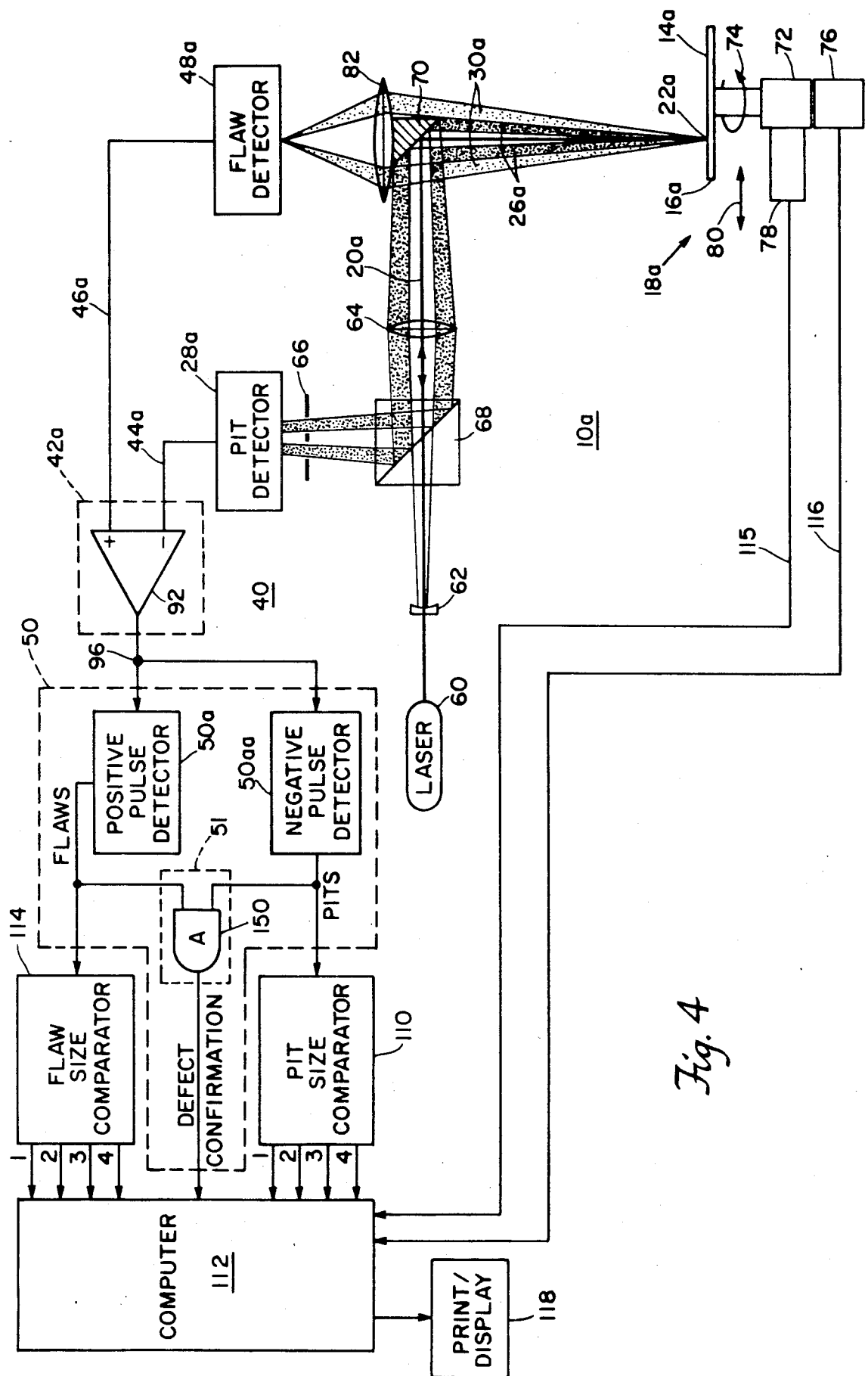
Figure 5:
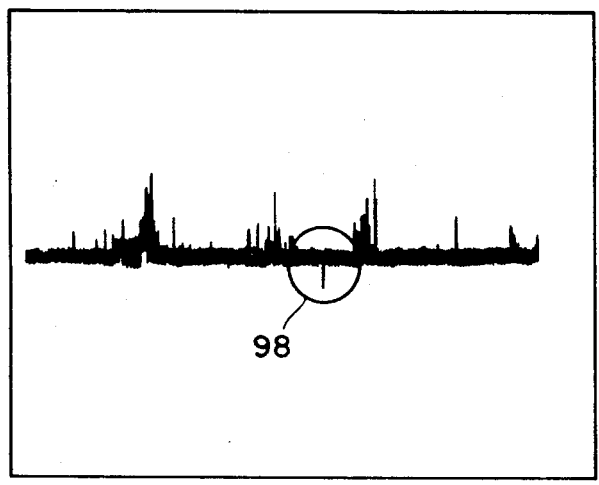
Figure 6:
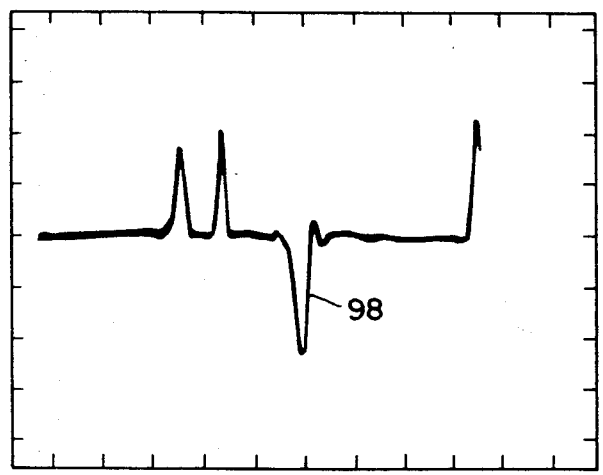
Figure 7:
Figure 9:
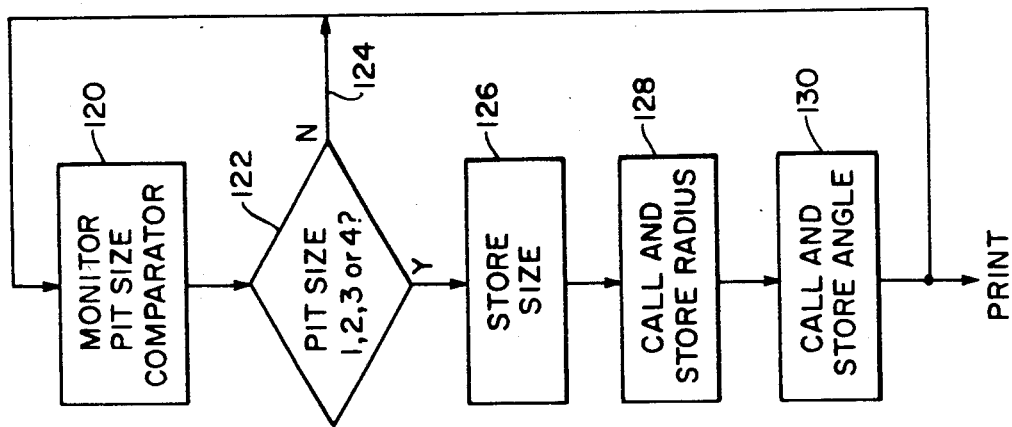
Figure 8:
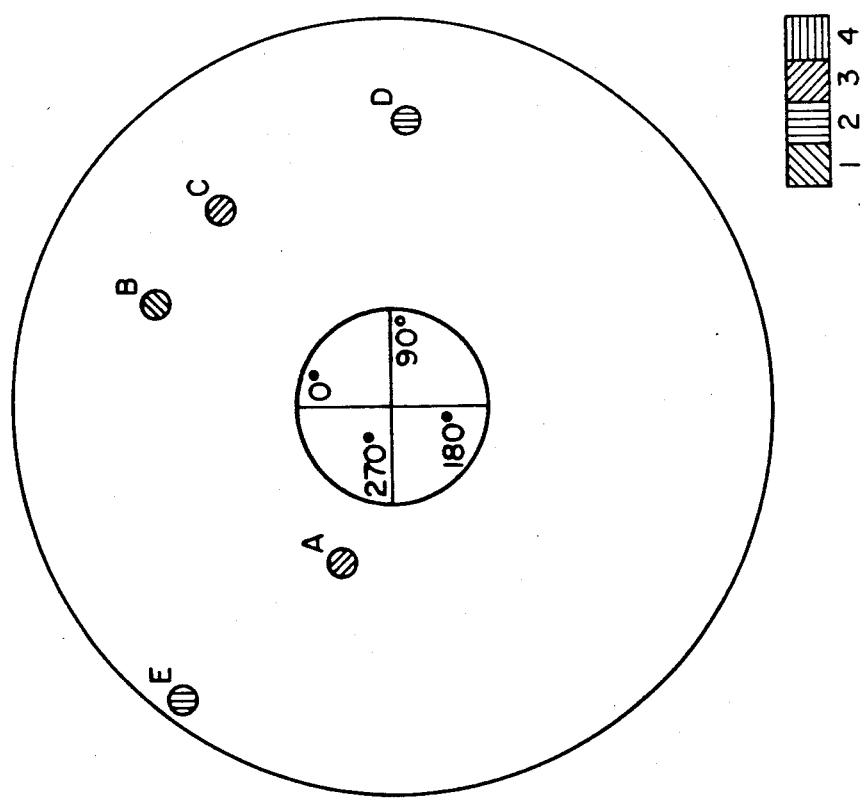

Other objects, features and advantages will occur from the following description of a preferred embodiment and the accompanying drawings, in which: FIG. 1 is a schematic diagram of an optical detection device according to this invention; FIG. 2 is a block diagram of a detection apparatus according to this invention; FIG. 3 is a top plan view showing the detectors of FIG. 1; FIG. 4 is a more detailed block diagram showing a system including an optical detection device and detection apparatus for defect/contamination distinction in accordance with this invention; FIG. 5 is a photograph of a normalized signal obtained from one complete rotation at a single radius of the surface to be inspected; FIG. 6 is an enlarged view of the circled portion of the signal in FIG. 5; FIG. 7 is an enlarged view of the pit signal and defect signal which are normalized to obtain the normalized signal in FIG. 6; FIG. 8 is a plan view showing a pit map of a disk produced by the system of this invention; and FIG. 9 is a flow chart showing the routine used to obtain the map of FIG. 8.

Because surface defects are the result of a major infraction on the surface, there is a local warping nearby the defect. The inventors, as taught in their copending application, "Surface Pit Detection System and Method", incorporated herein by reference, optimized the pit detection to the degree where minute surface depressions, like those accompanying surface flaws, are readily detectable. Normally, such high sensitivity to minute surface concave depression (or convex elevation) would be of no consequence since at this high sensitivity there are many such events on the surface and these are not considered defects.

Thus the detection of minute local warpings or pits on the surface under inspection is not significant by itself. However, recognizing that the presence of a minute local pit may indicate that a physical defect is nearby is significant, since this information can be used as a pointer to separate surface contamination from physical defects. That is, the coincident presence of a small pit signal, with a signal from the physical defect detector, identifies the surface event as a true physical defect.

Stated in another way: operating in the high-sensitivity mode, the pit detection optics can uniquely detect and distinguish pits or minute warping (concave or convex) on a noisy optical surface or where contamination is present. Physical flaws (scratches, gouges, pricks, etc.) tend to have boundaries that are minutely warped or pitted. Surface contamination, dust or other type particles do not fracture the surface and therefore do not have an association with surface warping or pits. Therefore, the pit detection provides a means for identifying the presence of a physical defect on a surface with extensive contamination. That is, the ANDing of the presence of a pit signal with the standard physical defect signal provides a composite signal which identifies a physical defect and ignores contamination.

There is shown in FIG. 1 an optical detection device 10 according to this invention which includes a means 12 for directing a beam of radiation onto the surface 14 to be inspected of a magnetic storage disk 16. Disk 16 is mounted for movement in two mutually perpendicular directions in the plane of the surface 14. In this way the spot 22 formed by beam 20 is made to move relative to surface 14. Since surface 14 is smooth, typically a highly polished or specular surface, it normally reflects the radiation of beam 20 back along beam 20. However, if a surface (concave/convex) depression or pit is encountered, light is scattered, not greatly into the far-specular region, but rather in the near-specular region as shown by volume 26, generally conical in shape and in the nature of a toroid where it approaches sensor 28. Other types of flaws such as defects, e.g. scratches, gouges, or contamination, e.g. dust, dirt, fingerprints, oil, also scatter the light but into the far-specular region such as indicated by toroidal conical volume 30. The realization that the surface depressions or pits scatter the light predominantly in the near-specular region enables the use of a sensor such as sensor 28 properly placed to be used to detect the occurrence of pits on surface 14. The further realization that pits accompany defects but not contamination enables the detection and distinguishing of defects from contamination. By near-specular region is meant an angle of approximately 40–100 milliradians. By far-specular region is meant an angle greater than 100 milliradians. While the beam 20 is shown as normal to surface 14, this is not necessary as any angle between grazing and normal would suffice. Mirror 32 is sized and positioned so that it directs beam 20 to surface 14 and with respect to the return radiation blocks virtually only the specular reflection from surface 14 while leaving the volume 26 surrounding it free to pass the near-specular scattered radiation.

The detector apparatus 40, FIG. 2, according to this invention includes a normalizing circuit 42 which receives the output from sensor 28 on line 44 representing the near-specular signal representative of a pit, and the signal on line 46 from a similar sensor 48 which provides a signal representative of the far-specular radiation in the conical volume 30. Typically the normalized circuit enhances the signal-to-noise ratio from approximately 2:1 to a range of 30–40:1. The output from nnormalizing circuit 42 is delivered to discriminator circuit 50 which detects the coincidence of the components of the normalized signal represents the near-specular and far-specular signals. The outputs from circuit 50 are received by defect detector 51 which indicates a defect upon coincidence of a pit and a flaw indication.

A top view of sensors 28 and 48 of FIG. 1 is shown in FIG. 3, where the toroidal shape is readily apparent.

In a preferred construction, FIG. 4, optical detection device 10a includes a light source which may be but need not be a collimated, coherent light source such as laser 60, whose output is fed through beam expander 62 and then focussing lens 64 to create beam 20a which strikes corner mirror 70. The beam is then reflected down to a spot 22a on the surface 14a of disk 16a. Disk 16a is mounted on an air spindle 72 which rotates disk 14a as indicated by arrow 74. An encoder 76 monitors and controls the rotation of air spindle 72. A servo drive 78 moves air spindle 72 in a translational manner back and forth in the direction shown by arrow 80. Some of the radiation striking a surface depression or pit at spot 22a is reflected, in the near-specular region 26a. Radiation in this region encounters the surface of corner mirror 70 and is reflected back to the surface of beam splitter 68 and forwards the pit detector 28a. The specular reflection and scattered radiation in the near-specular region 26a are redirected toward the spatial filter 66 which blocks the specular reflection to the scattered radiation in the near-specular region 26a passes on to the pit detector 28a which provides a signal indicative of the near-specular region radiation.

If at spot 22a there is another type of flaw as well, e.g. a defect or contamination, then the radiation returns primarily in the far-specular region 30a, which surrounds and avoids corner mirror 70 and instead is focussed by lens 82 on flaw detector 48a which provides a signal representative of the light scattered in the far-specular region.

There are many oteer constructions which can be used in place of the optical detector 10a, FIG. 4. For example, beam splitter 68 can be a mirror with a hole centered around the illuminating beam 20a to further restrict the light and enhance the signal-to-noise ratio.

The signal representative of the near-specular region and the pits is fed on line 44a to the negative input of amplifier 92, while the signal representative of the far-specular region radiation indicative of other defects is fed on line 46a to the positive input of amplifier 92. In amplifier 92 the two signals are algebraically summed: that is, the pit signal is subtracted from the flaw signal and the resultant signal is provided at the output to positive pulse detector 50a and negative pulse detector 50aa. The normalized output of amplifier 92 for one complete rotation of disk 16a at a single fixed radius is shown in FIG. 5. This is the signal that appears at junction 96 in FIG. 4. The single negative pulse 98 represents a pit. The multitude of positive-going background pulses represent any one of a number of other flaws, including defects and contamination, and noise.

An enlargement of the circled area in FIG. 5 is shown in FIG. 6, where the negative-going pulse 98 is more clearly shown along with the neighboring positive-going pulses. The section of the normalized signal shown in FIG. 6 is formed from the two signals shown in FIG. 7. The upper trace is the pit signal on line 44a from pit detector 28a. The lower trace is the output on line 46a from flaw detector 48a. It is the summation of these two signals that produce the signal shown in FIG. 6. It can be seen that the peak 98 in the upper trace of FIG. 7 is detected as quite large in the near-specular radiation, while the same pit produces a much lower peak 98' in the lower trace. This verifies that the dominant radiation scattering for pits occurs in the near-specular region, not the far.

With the signal of FIG. 5 present at junction 96, negative pulse detector 50a, which may be a rectifier or diode, easily detects the pit 98 and provides a signal representative thereof to the pit size comparator 110. The pit size comparator classifies the signal into one of four sizes and indicates that size to computer 112. Positive pulse detector 50a may be provided to similarly detect positive-going peaks representative of other flaws on the surface which may be delivered to a flaw size comparator 114 which classifies the signal in a similar way and delivers it to computer 112. The amplitude of the pit signal delivered to pit size comparator 110 is determined in part by the curvature (convex/concave) of the pit. With this system, pits as small as 5 $\mu$ may be detected and other defects as small as 0.5$\mu$ may be detected. In comparison, an operator with even the best eyesight can see pits only as small as approximately 10–20$\mu$ and other defects only as small as approximately 3–5$\mu$.

Computer 112 drives servo device 78 and receives positional input from it over line 115, and drives encoder 76 and receives positional information from it on line 116 so that a printout or display may be provided at 118, which indicates the radius and angle at which a pit was found and the size of the pit classified from 1 through 4. For example, a typical printout for a pit derived from pit size comparator 110 appears as follows:

| # | RADIUS (mils) | THETA (deg.) | Size |
| --- | --- | --- | --- |
| 1 | 802.00 | 289 | 4 |
| 2 | 802.50 | 289 | 4 |
| 3 | 802.50 | 289 | 4 |
| 4 | 803.00 | 289 | 4 |
| 5 | 803.00 | 289 | 4 |
| 6 | 803.50 | 289 | 4 |
| 7 | 803.50 | 289 | 4 |
| 8 | 804.00 | 289 | 4 |
| 9 | 804.50 | 289 | 1 |
| 10 | 1259.00 | 23 | 1 |
| 11 | 1259.00 | 49 | 2 |
| 12 | 1259.50 | 49 | 1 |
| 13 | 1368.50 | 94 | 2 |
| 14 | 1369.00 | 94 | 2 |
| 15 | 1801.00 | 306 | 1 |

It can be seen from this chart that the multiple pit detections 1–9 indicate a single pit at an angle of 289° (pit A) which extends from a radius of 802 mils to 804.5. Single pits are also indicated by multiple pit detections 11 and 12 (pit C) and pit detections 13 and 14 (pit D). Single pits are indicated by single pit detection #10 (pit B), and pit detection #15 (pit E). The numbers #10 and #15 refer to the chart shown above. For further convenience, the pit detections may be displayed on a map of the disk surface as shown in FIG. 8, where each of the circles represents a detected pit and the crosshatching indicates the size, 1, 2, 3 or 4, as indicated by the key in the lower right-hand corner of FIG. 9. The chart and the mapping in FIG. 8 may be simply accomplished with computer 112 by programming it to effect a routine such as shown in FIG. 9, where the computer in step 120 constantly monitors the pit size comparator 110. If the pit size does not reach a level 1 in step 122, then the system is rerouted on line 124 back to the input of step 120. If a pit size of 1 or larger is encountered, the computer then in step 126 orders that the size be stored and that the present radius and angle be called and stored in steps 128 and 130. This information can then later be printed out as in the chart or in the map of FIG. 8 and then attached to the inspected workpiece to accompany it through the rest of the manufacturing process.

In accordance with this invention, AND gate 150 or another coincidence detecting device receives the output from detector 50a indicating a flaw of some sort is present and the output of detector 50aa indicating that a pit or prick is present. Now when a flaw is detected, AND gate 150 provides a signal confirming that the flaw is indeed a defect, not just contamination. If there is no coincidence then the flaw is not a defect but some other type of flaw such as contamination, and there is no confirmation of the flaw a defect. Certainly if the comparators 110, 114 and/or the computer 112 is not required the output of the AND gate 150 may be utilized independently.

The apparatus disclosed illustrates one implementation for the method of this invention. According to the method, a beam of radiation is directed to a surface to be inspected. The radiation scattered from the surface is sent to the near-specular region and the far-specular region to produce signals representative thereof. The near-specular signal is normalized with respect to the far-specular signal. The near-specular components of the normalized signal are then discriminated to provide signals representative of surface pits.

Although specific features of this invention are shown in some drawings and not others, this is for convenience only as each feature may be combined with any or all of the other functions in accordance with the inention.

Other embodiments will occur to those skilled in the art and are within the following claims:

What is claimed is:

1. A surface defect detection and confirmation system comprising:
   means for directing a beam of radiation to a surface;
   means for separately sensing radiation scattered from the surface in the near-specular region indicative of a pit and in the far-specular region indicative of a flaw and producing signals representative thereof;
   means, responsive to said means for sensing, for normalizing the near-specular pit signal with respect to the far-specular flaw signal;
   means, responsive to said means for normalizing, for discriminating the near-specular components of said normalized signal; and
   means, responsive to said means for discriminating, for indicating that the flaw is a defect and not contamination upon coincidence of a pit signal and a flaw signal.

2. The system of claim 1 in which said means for directing includes lens means and a radiation source.

3. The system of claim 2 in which said radiation source provides a collimated beam.

4. The system of claim 2 in which said radiation source provides a coherent beam.

5. The system of claim 2 in which said radiation source is a laser.

6. The system of claim 1 further including means for providing relative motion between said beam and the surface.

7. The device of claim 6 in which said means for providing relative motion moves said beam and surface in two directions relative to one another.

8. The device of claim 7 in which said means for providing relative motion includes means for rotating said surface and translating said surface relative to said beam.

9. The system of claim 1 in which said means for separately sensing includes a first sensor for sensing near-specular radiation and a second sensor for sensing far-specular radiation.

10. The system of claim 1 in which said means for normalizing includes a comparator.

11. The system of claim 10 in which said comparator receives said near-specular signal as a first polarity and said far-specular signal as a second opposite polarity and sums the signals.

12. The system of claim 10 in which said comparator subtracts said far-specular signal from said near-specular signal.

13. The system of claim 11 in which said means for discriminating further includes a first detector circuit for detecting components of said first polarity of said normalized signal.

14. The system of claim 13 in which said means for discriminating includes a second detector circuit for detecting components of said second polarity of said normalized signal.

15. The system of claim 1 in which said means for indicating includes an AND gate.

16. The system of claim 14 in which said means for indicating includes an AND gate responsive to said first and second detector circuits.

17. A method of surface defect detection and confirmation comprising:
  irradiating an area of a surface;
  separately sensing radiation scattered from the surface in the near-specular region indicative of a pit and in the far-specular region indicative of a flaw, and producing signals representative thereof;
  normalizing the near-specular signal with respect to the far-specular signal;
  discriminating the near-specular pit component from the normalized signal; and
  indicating that the flaw is a defect and not contamination upon coincidence between the pit signal and flaw signal.

* * * * *